United States Patent [19]

Baker et al.

[11] E Patent Number: Re. 32,196

[45] Reissued Date of Patent: Jul. 1, 1986

[54] AURONE DERIVATIVES

[75] Inventors: Stephen R. Baker, Eversley; William B. Jamieson, Woking; William J. Ross, Lightwater, all of England

[73] Assignee: Lilly Industries Limited, London, England

[21] Appl. No.: 379,793

[22] Filed: May 19, 1982

Related U.S. Patent Documents

Reissue of:

[64] Patent No.: 4,259,340
Issued: Mar. 31, 1981
Appl. No.: 71,515
Filed: Aug. 31, 1979

[30] Foreign Application Priority Data

Sep. 13, 1978 [GB] United Kingdom ..... 36705/78

[51] Int. Cl.[4] ..... C07D 307/83; C07D 405/02

[52] U.S. Cl. ..... 514/382; 514/470; 514/826; 548/253; 549/458; 549/466

[58] Field of Search ..... 542/441; 424/285, 269; 514/382, 470, 826; 548/253; 549/458, 466

[56] References Cited

U.S. PATENT DOCUMENTS

| | | | |
|---|---|---|---|
| 3,716,531 | 2/1973 | Albrecht et al. | 542/441 |
| 3,975,380 | 8/1976 | Snader et al. | 542/441 |
| 4,067,993 | 1/1978 | Scherrer | 424/285 |
| 4,083,952 | 4/1978 | Snader et al. | 424/285 |
| 4,115,567 | 9/1978 | Doria et al. | 345.2/ |
| 4,143,055 | 3/1979 | Ocelli | 424/285 |
| 4,143,145 | 3/1979 | Doria et al. | 260/345.2 |

FOREIGN PATENT DOCUMENTS

| | | |
|---|---|---|
| 873826 | 1/1979 | Belgium . |
| 2829619 | 1/1979 | Fed. Rep. of Germany . |
| 2001631 | 2/1979 | United Kingdom . |
| 2014566 | 8/1979 | United Kingdom . |

OTHER PUBLICATIONS

Nagao, Chem. Pharm. Bull., 20 (1972), pp. 82–87.
Flandre, Soc. Biol. Montpellier, 1976, pp. 146–150.
Castel et al., Trav. Soc. Pharm. Montpellier, 36 (1976) pp. 239–246.
Derwent Abstract, #29852.

*Primary Examiner*—Arthur P. Demers
*Attorney, Agent, or Firm*—Charles W. Ashbrook; Arthur R. Whale

[57] ABSTRACT

Substituted aurones of formula (I):

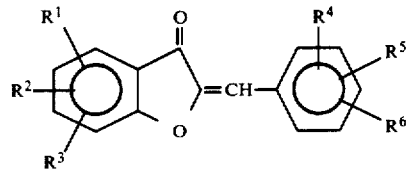

(I)

wherein $R^1$, $R^2$, $R^3$, $R^4$, $R^5$ and $R^6$ are the same or different and can each represent hydrogen, halogen, $C_{1-6}$alkyl, $C_{1-6}$alkoxy, $C_{3-8}$cycloalkyl, optionally substituted phenyl, $C_{1-6}$ haloalkyl, amido, amino, cyano, hydroxy, nitro, $C_{2-4}$ alkenyl, carboxyl, tetrazol-5-yl and —CH=CHCOOH; or wherein $R^1$ and $R^2$ taken together can represent a group of formula —CH=CH—CH=CH— provided that at least one of $R^1$, $R^2$, $R^3$, $R^4$, $R^5$ and $R^6$ is carboxyl, tetrazol-5-yl or —CH=CHCOOH;

or a pharmaceutically-acceptable salt or ester thereof, are effective in the prophylactic chemotherapy of allergic conditions such as bronchial asthma.

16 Claims, No Drawings

AURONE DERIVATIVES

Matter enclosed in heavy brackets [ ] appears in the original patent but forms no part of this reissue specification; matter printed in italics indicates the additions made by reissue.

This invention relates to novel aurone derivatives possessing valuable pharmacological activity, a process for their production and their use as pharmaceuticals.

In recent years, extensive efforts have been made to discover new compounds useful in the alleviation of allergic diseases and there is, in particular, a need for therapeutic agents which are effective in treating immediate hypersensitivity conditions such as asthma.

We have discovered certain aurone derivatives possessing the following basic skeleton, which have such useful activity.

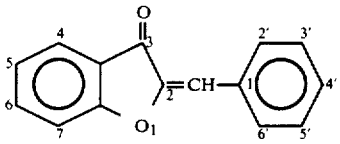

According to the present invention there is provided a substituted aurone of formula I

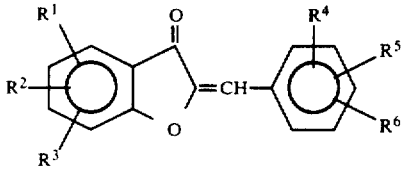

I in which $R^1$, $R^2$, $R^3$, $R^4$, $R^5$ and $R^6$ are the same or different and can each represent hydrogen, halogen, $C_{1-6}$ alkyl, $C_{1-6}$ alkoxy, $C_{3-8}$ cycloalkyl, optionally substituted phenyl, $C_{1-6}$ haloalkyl, amido, amino, cyano, hydroxy, nitro, $C_{2-4}$ alkenyl, carboxyl, tetrazol-5-yl or —C=CHCOOH; or in which $R^1$ and $R^2$ taken together respresent a group of formula —CH=CH—CH=CH—; provided that at least one of $R^1$, $R^2$, $R^3$, $R^4$, $R^5$ and $R^6$ is carboxyl, tetrazol-5-yl or —CH=CHCOOH; or a pharmaceutically-acceptable salt or ester thereof.

The compounds of formula I may exist in the (E)— or (Z)— form, the (Z)— form being preferred.

A more particular group of compounds is one of formula (I) in which $R^1$, $R^2$, $R^3$, $R^4$, $R^5$ and $R^6$ have the values defined above provided that when $R^1$, $R^2$ and $R^3$ are all hydrogen at least one of $R^4$, $R^5$ and $R^6$ is tetrazol-5-yl or —CH=CHCOOH. It is preferred that the benzofuranone ring be substituted and thus a preferred group is one of formula (I) in which at least one of $R^1$, $R^2$ and $R^3$ is other than hydrogen.

A further particular group of compounds is one of formula (I) in which $R^1$, $R^2$, $R^3$, $R^4$, $R^5$ and $R^6$ have the values defined above provided that when one of $R^1$, $R^2$ and $R^3$ is carboxyl at least one of $R^4$, $R^5$ and $R^6$ is halogen, $C_{3-8}$ cycloalkyl, optionally substituted phenyl, $C_{1-6}$ haloalkyl, amido, cyano, nitro, carboxyl, tetrazol-5-yl or —CH=CHCOOH. It is frequently preferred that at least one of the substituents on the free benzene ring is one such substituent and thus a preferred group is one of formula (I) in which at least one of $R^4$, $R^5$ and $R^6$ is halogen, $C_{3-8}$ cycloalkyl, optionally substituted phenyl, $C_{1-6}$ haloalkyl, amido, cyano, nitro, carboxyl, tetrazol-5-yl or —CH=CHCOOH.

An especially preferred group of compounds is one of formula (I) in which at least one of $R^1$, $R^2$ and $R^3$ is other than hydrogen and at least one of $R^4$, $R^5$ and $R^6$ is halogen, $C_{3-8}$ cycloaklyl, optionally substituted phenyl, $C_{1-6}$ haloalkyl, amido, cyano, nitro, carboxyl, tetrazol-5-yl or —CH=CHCOOH.

The term "halogen" means especially chlorine, bromine and fluorine. The term "$C_{1-6}$ alkyl" includes, for example, methyl, ethyl, propyl, isopropyl, butyl, tert butyl, pentyl and hexyl, being preferably methyl, ethyl or tert-butyl. The term "$C_{1-6}$ alkoxy" includes, for example, methoxy, ethoxy, propoxy, butoxy and is preferably methoxy. The term "$C_{3-8}$ cycloalkyl" is preferably cyclohexyl. The term "optionally substituted phenyl" includes, for example, phenyl optionally substituted with 1 to 3 substituents selected from methyl, methoxy, halogen and nitro. The term "$C_{1-6}$ haloalkyl" can be, for example, any of the groups listed for "$C_{1-6}$ alkyl" substituted with one to three halo atoms such as fluorine or chlorine and is especially trifluoromethyl. The term "$C_{2-4}$ alkenyl" is preferably allyl. It is preferred that $R^1$, $R^2$, $R^3$, $R^4$, $R^5$ and $R^6$ be selected from hydrogen, halogen, $C_{1-4}$ alkyl, $C_{1-4}$ alkoxy, cyclohexyl, trifluoromethyl, N-isopropylcarboxamido, acetamido, dimethylamino, hydroxy, carboxyl, tetrazol-5-yl or —CH=CHCOOH, or $R^1$ and $R^2$ together represent —CH=CH—CH=CH—.

Other preferred compounds falling within the scope of the aurones of formula (I) are those compounds having one or more of the following characteristics:

(a) $R^1$ is $C_{1-4}$ alkyl such as methyl
(b) $R^1$ is $C_{1-4}$ alkoxy such as methoxy
(c) $R^1$ is halogen such as chlorine
(d) $R^1$ is $C_{3-8}$ cycloalkyl such as cyclohexyl
(e) $R^1$ amino
(f) $R^1$ is carboxyl
(g) $R^1$ is a 5- or 6-substituent
(h) $R^1$ is hydroxyl
(i) $R^2$ is hydrogen
(j) $R^3$ is hydrogen
(k) $R^4$ is carboxyl
(l) $R^4$ is tetrazol-5-yl
(m) $R^4$ is —CH=CHCOOH
(n) $R^5$ is hydrogen
(o) $R^6$ is hydrogen A particularly preferred group of compounds is one in which $R^1$ is $C_{1-4}$ alkyl, carboxyl or halogen, $R^2$ and $R^3$ are hydrogen, $R^4$ is carboxyl or —CH=CHCOOH and $R^5$ and $R^6$ are hydrogen. Of this group, the compounds in which $R^1$ is alkyl or carboxyl, $R^2$ and $R^3$ are hydrogen, $R^4$ is carboxyl or —CH=CHCOOH and $R^5$ and $R^6$ are hydrogen are most preferred.

The compounds of formula I can also be in the form of their pharmaceutically-acceptable salts or esters. Such derivatives are encountered, for example, when one or more of the substituents $R^1$, $R^2$, $R^3$, $R^4$, $R^5$ and $R^6$ are the acid function, carboxyl or —CH=CHCOOH. Suitable salts include for example those of mineral bases such as alkali metal hydroxides, especially the potassium or sodium salts, or alkaline earth metal hydroxides, especially the calcium salts, or of organic bases such as amines. Preferred esters are those derived from $C_{1-4}$ alkanols, for example, the methyl, ethyl, propyl, isopropyl, butyl, t-butyl, methoxyethyl or ethoxyethyl esters.

The invention also includes a method of preparing aurones of formula (I) which comprises reacting a benzaldehyde of formula (III)

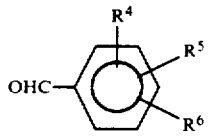

III with (a) a benzofuranone of formula (IV)

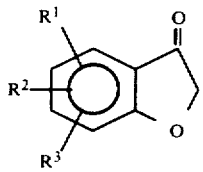

IV or (b) an ω-substituted acetophenone of formula (V)

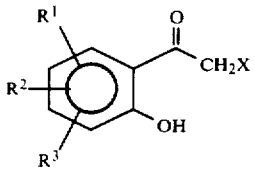

V i which X is a leaving group; optionally followed when one or more of $R^1$, $R^2$, $R^3$, $R^4$, $R^5$ or $R^6$ is cyano by reaction with an azide to give the corresponding tetrazol-5-yl compound.

As indicated above, aurones of formula (I) may be prepared by condensing an appropriately substituted benzaldehyde (III) with a benzofuranone derivative (IV) as schematically depicted below:

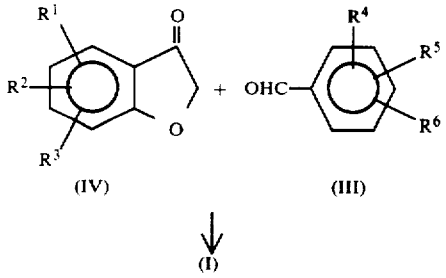

Suitable solvents for this reaction include ethereal solvents such as dioxan and tetrahydrofuran and liquid alkanols such as ethanol. In general, temperature is not critical and is only determinative of the reaction rate. The reaction will proceed at all temperatures between ambient and the reflux temperature of the reaction mixture, for example, between 25° and 150° C. The reaction is preferably acid or base catalysed. Suitable acid catalysts include mineral acids such as hydrochloric acid and strong organic acids such as p-toluene sulphonic acids, whereas suitable inorganic or organic base catalysts include alkalies such as caustic soda, caustic potash, sodium carbonate or triethylamine. This type of condensation reaction is well known and those skilled in the art will well appreciate the nature of the reaction conditions and reagents necessary to produce a particular aurone of the formula (I)

An alternative process for preparing compounds of formula (I) involves the reaction of an ω-substituted acetophenone (V) with an appropriate benzaldehyde (III) as depicted schematically below:

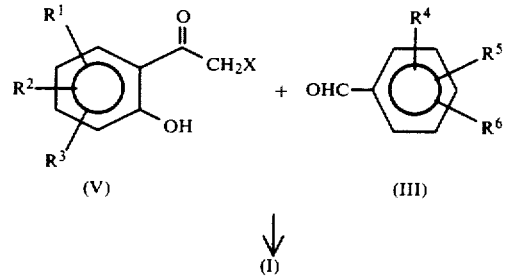

where X is a leaving group, such as for example halogen, especially chloride or bromide, or the tosyl group. Suitable solvents include ethereal solvents such as dioxan and tetrahydrofuran and liquid alkanols such as ethanol. In this instance the reaction is preferably base catalysed using a catalyst such as caustic soda, caustic potash or sodium carbonate. Temperatures from 0° to 150° C. can be used to effect the reaction. The reactants of formula (III), (IV) and (V) are in the main known compounds and can be prepared by well known routes described in the literature.

In addition, compounds of formula (I) in which one of the R groups is tetrazol-5-yl can be derived by preparing the corresponding nitrile and forming the tetrazole therefrom utilising a preferably non-nucleophilic azide, for example trimethylsilyl azide, in a high boiling solvent such as dimethylformamide at temperatures above 100° C.

These reactions will produce the (Z)-isomer which, if desired, can be converted to the corresponding (E)-isomer by photolytic methods which are well known in the art.

The aurones of formula (I) have been shown to be useful in the propylactic treatment of asthma in mammals. This activity has been demonstrated in guinea pigs using either the "Herxheimer" test described in the Journal of Physiology (London) 7, 251 (1952) or the "guinea-pig chopped lung test" described by Mongar and Schild in the Journal of Physiology (London) 3, 207 (1956) or Brocklehurst Journal of Physiology (London) 52, 414 (1960). Compounds are also active in the "rat peritoneal anaphylaxis test" based on allergic reaction in the peritoneal cavity of the rat, as described by Orange, Stechschulte and Austen in Fed. Proc. 28 1710 (1969).

The "Herxheimer" test is based on an allergic bronchospasm induced in guinea pigs which closely resembles an asthamatic attack in man. The mediators causing the bronchospasm are very similar to those released when sensitised human lung tissue is challenged with an antigen. Compounds of the invention have exhibited activity in the "Herxheimer" test at dosages ranging from 25 mg/kg to 200 mg/kg.

The compounds of formula (I) may be administered by various routes and for this purpose may be formulated in a variety of forms, although it is a special feature of the compounds of the invention that they are effective when administered orally. Thus the compounds of the invention may be administered by the oral and rectal routes, topically, parenterally, e.g. by injection, in the form of, for example, tablets, lozenges, sublingual tablets, sachets, cachets, elixers, suspensions, aerosols, ointments, for example, containing up to 10% by weight of the active compound in a suitable base, soft and hard gelatin capsules, suppositories, injection solutions and suspensions in physiologically acceptable media, and sterile packaged powders absorbed onto a support material for making injection solutions. The nature of the various excipients and additives required to produce such formulations will be well-known to those skilled in the art.

However, some examples of excipients which may be employed in the pharmaceutical formulations of the present invention are lactose, dextrose, sucrose, sorbitol, mannitol, propylene glycol, liquid paraffin, white soft paraffin, kaolin, fumed silicon dioxide, microcrystalline cellulose, calcium silicate, silica, polyvinylpyrrolidone, cetostearyl alcohol, starch, modified starches, gum acacia, calcium phosphate, cocoa butter, ethoxylated esters, oil of theobroma, arachis oil, alginates, tragacanth, gelatin, syrup B.P., methyl cellulose, polyoxyethylene sorbitan monolaurate, ethyl lactate, methyl and propyl hydroxybenzoate, sorbitan trioleate, sorbitan sesquioleate and oleyl alcohol and propellants such as trichloromonofluoromethane, dichlorodifluoromethane and dichlorotetrafluoroethane. In the case of tablets, a lubricant may be incorporated to prevent sticking and binding of the powdered ingredients in the dies and on the punch of the tabletting machine. For such purpose there may be employed for instance aluminium, magnesium or calcium stearates, talc or mineral oil.

The invenion also includes a pharmaceutical formulation which comprises as an active ingredient a compound of formula (I) or a pharmaceutically-acceptable salt or ester thereof, associated with a pharmaceutically-acceptable carrier therefor. Pharmaceutical formulations can be provided in dosage unit form, each dosage unit preferably containing from 5 to 500 mg. (from 5.0 to 50 mg. in the case of parenteral administration, from 5.0 to 50 mg. in the case of inhalation and from 25 to 500 mg. in the case of oral or rectal administration) of a compound of formula (I). The term "unit dosage form", as used in the specification and claims, refers to physically discrete units suitable as unitary dosages for human subjects and animals, each unit containing a predetermined quantity of active material calculated to produce the desired therapeutic effect in association with the required pharmaceutical diluent, carrier or vehicle.

Dosages of from 0.5 to 200 mg/kg per day, preferably 1 to 20 mg/kg of active ingredient may be administered, although it will, of course, be understood that the amount of the aurone of formula (I) actually administered will be determined by a physician, in the light of the revelent circumstances including the condition to be treated, the choice of compound to be administered and the chosen of route of administration and therefore the above preferred dosage range is not intended to limit the scope of the present invention in any way.

The following Examples illustrate the invention.

EXAMPLE 1

(Z)-4'-Carboxyl-2-benzylidene-5-methylbenzofuran-3(2H)-one

ω-Chloro-2-hydroxy-5methylacetophenone (8.73 g, 0.05 mole) [Chem. Ber 41, 4271, (1908)] and 4-carboxybenzaldehyde (7.5 g, 0.05 mole) were dissolved in ethanol (100 ml) and the mixture heated to 60° C. Sodium hydroxide (4 g, 0.1 mole) in water (20 ml) was then slowly added to the stirred mixture which turned deep red. After 1 hour at 60° C. a pale yellow precipitate formed which was then refluxed for a further hour. The suspension so formed was then cooled to 0° C. and acidified with hydrochloric acid (5 M). The resultant pale yellow solid was filtered off, washed with water, dried under reduced pressure and recrystallised from dioxan to yield the title compound as pale yellow needles, m.p. 288°-290° C. (decomp.)

EXAMPLES 2 TO 5

The following compounds were similarly prepared using the appropriate benzaldehyde and chloroactophenone.

(Z)-2'-Carboxyl-2-benzylidene-5-methylbenzofuran-3(2H)-one, m.p, 187°-189° C.

(Z)-2'-Carboxyl-2-benzylidene-6-methylbenzofuran-3(2H)-one, m.p. 196°-198° C. (decomp.)

(Z)-2'-Carboxyl-2-benzylidenenaptho(2,1-b)furan-3(2H)-one, m.p. 207°-208° C.

(Z)-4'-Carboxyl-2-benzylidene-5-isopropylbenzofuran-3(2H)-one, m.p. 262°-263° C.

EXAMPLE 6

(Z)-3'-Carboxyl-2-benzylidene-5-methoxybenzofuran-3(2H)-one

5-Methoxybenzofuran-3(2H)-one (6.0 g, 0.036 mole) [Annalen 405, 281, (1914)] and 3-carboxybenzaldehyde (5.4 g, 0.036 mole) [J. Chem Soc. 4778 (1952)] were dissolved in dioxan (50 ml) and concentrated hydrochloric acid (10 ml) added. The resultant yellow solution was then heated under reflux for 2 hours. On cooling and addition of water (20 ml) a yellow precipitate formed. This material on recrystallization from acetic acid yielded the title compound as yellow needles, m.p. 252°-254° C.

EXAMPLES 7 TO 36

The following compounds were prepared using a process similar to that of Example 6 with appropriate variation of the benzofuranone and benzaldehyde.

(Z)-2'-Carboxyl-2-benzylidene-6-methoxybenzofuran-3(2H)-one, m.p. 217°-220° C. (decomp).

(Z)-3'-Carboxyl-2-benzylidene-6-methoxybenzofuran-3(2H)-one, m.p. 258°-260° C. (decomp.)

(Z)-4'-Carboxyl-2-benzylidene-6-methoxybenzofuran-3(2H)-one, m.p. 273°-275° C. (decomp.)

(Z)-3'-Carboxyl-2-benzylidene-5-methylbenzofuran-3(2H)-one, m.p. 264°-265° C.

(Z)-3'-Carboxyl-2-benzylidene-6-methylbenzofuran-3-(2H)-one, m.p. 263°-264° C.

(Z)-4'-Carboxyl-2-benzylidene-6-methylbenzofuran-3(2H)-one, m.p. 288°-289° C.

(Z)-3'-Carboxyl-4'-hydroxy-2-benzylidene-6-methylbenzofuran-3(2H)-one m.p. 290°-291° C.

(Z)-3'-Carboxyl-4'-hydroxy-2-benzylidenebenzofuran-3(2H)-one, m.p. 268°-270° C.

(Z)-4'-Carboxyl-2-benzylidenebenzofuran-3(2H)-one, m.p. 274°-275° C.

(Z)-3'-Carboxyl-2-benzylidene-6-chlorobenzofuran-3(2H)-one, m.p. 278°-280° C.

(Z)-2'-Carboxyl-2-benzylidene-5-chlorobenzofuran-3(2H)-one, m.p. 205°-206° C.

(Z)-3'-Carboxyl-2-benzylidene-5-chlorobenzofuran-3(2H)-one, m.p. 286°-288° C.

(Z)-4'-Carboxyl-2-benzylidene-5-chlorobenzofuran-3(2H)-one, m.p. 300° C.

(Z)-3'-Carboxyl-2-benzylidene-5-ethylbenzofuran-3(2H)-one, m.p. 252° C.

(Z)-3'-Carboxyl-2-benzylidenebenzofuran-3(2H)-one, m.p. 259°-260° C.

(Z)-4'-[(E)-Carboxyvinyl]-2-benzylidene-5-methylbenzofuran-3(2H)-one, m.p. 275°-276° C.

(Z)-3'-Carboxyl-2-benzylidene-5-cyclohexylbenzofuran-3(2H)-one, m.p. 252°-253° C.

(Z)-4'-Carboxyl-2-benzylidene-6-chlorobenzofuran-3(2H)-one, m.p. 300° C.

(Z)-2'-Carboxyl-2-benzylidene-6-chlorobenzofuran-3(2H)-one, m.p. 184° C.

(Z)-4'-[(E)-2-Carboxyvinyl]-2-benzylidene-6-hydroxybenzofuran-3(2H)-one, m.p. 300° C. (decomp.)

(Z)-3'-Carboxyl-2-benzylidene-6-hydroxybenzofuran-3(2H)-one, m.p. 320° C. (decomp.)

(Z)-2'-Carboxyl-2-benzylidene-6-hydroxybenzofuran-3(2H)-one, m.p. 282°-283° C.

(Z)-4'-[(E)-2-Carboxyvinyl]-2-benzylidene-5,7-dichlorobenzofuran-3(2H)-one, m.p. 300° C.

(Z)-3'-[(E)-2-Carboxyvinyl]-2-benzylidene-5,7-dichlorobenzofuran-3-(2H)-one m.p. 300° C.

(Z)-3'-[(E)-2-Carboxyvinyl]-2-benzylidene-6-hydroxybenzofuran-3-(2H)-one, m.p. 300° C.

(Z)-3'-[(E)-2-Carboxyvinyl]-2-benzylidene-5-methoxybenzofuran-3-(2H)-one, m.p. 242° C.

(Z)-3'-Carboxyl-2-benzylidenenaphtho(1,2-b)furan-3(2H)-one, m.p. 276°-278° C.

(Z)-3'-[(E)-2-Carboxyvinyl)]-2-benzylidenenaphtho-(1,2-b)furan-3(2H)-one, m.p. 280° C.

(Z)-3'-Carboxyl-2-benzylidene-4-hydroxybenzofuran-3(2H)-one, m.p. 285°-287° C.

(Z)-2'-Carboxyl-2-benzylidene-5,7-dibromo-4-hydroxybenzofuran-3(2H)-one, m.p. 258°-260° C.

EXAMPLE 37

(Z)-4'-(5-Tetrazolyl)-2-benzylidene-5-chlorobenzofuran-3-(2H)-one

4-Cyanobenzaldehyde (13.1 g, 0.1 mole), ethyleneglycol (6.2 g 0.1 mole) and toluene-4-toluene-4-sulphonic acid (19.0 mg, 0.1 m. mole) were refluxed in benzene (100 ml) for 8 hours using a Dean and Stark apparatus. The benzene was then evaporated to dryness to give 4-cyano-(2-1,3 dioxalane) benzene as a waxy colourless solid (m.p. 44°-45° C.) which was used without further purification.

The above dioxalane (17.1 g, 0.1 mole), sodium azide (6.5 g, 0.1 mole) and lithium chloride (6.5 g, 0.15 mole) were refluxed in 2-methoxyethanol (100 ml) for 8 hours. The suspension was then poured into ice and hydrochloric acid (5 M). On standing, this solution deposited white crystals of 4-(5-tetrazolyl)-benzaldhyde, m.p. 200° C.

This benzaldehyde and 5-chlorobenzofuran-3(2H)-one [Annalen 2924 405 346] were reacted together using the procedure of Example 6 to yield the title compound which was recrystallised from dimethylformamide, m.p. 260° C. (decomp).

EXAMPLES 38 TO 41

The following compounds were similarly prepared using the appropriate cyanobenzaldhyde and benzofuranone.

(Z)-3'-(5-Tetrazolyl)-2-benzylidene-5-methoxybenzofuran-3(2H)-one, m.p. 278°-280° C. (decomp.)

(Z)-4'-(5-Tetrazolyl)-2-benzylidene-6-hydroxybenzofuran-3(2H)-one, m.p. 300° C. (decomp.)

(Z)-4'-(5-Tetrazolyl)-2-benzylidene-5-methoxybenzofuran-3(2H)-one, m.p. 268°-270° C. (decomp.)

(Z)-3'-(5-Tetrazolyl)-2-benzylidene-5,7-dichlorobenzofuran-3(2H)-one, m.p. 283°-285° C. (decomp)

EXAMPLE 42

(Z)-3'-(5-Tetrazolyl)-2-benzylidene-5-ethylbenzofuran-3(2H)-one

5-Ethylbenzofuran-3(2H)-one (3.4 g, 0.02 mole) [J. Indian Chem. Soc. 42, 20 (1965)] and 3-cyanobenzaldehyde (2.62 g, 0.02 mole) were dissolved in dioxan (100 ml) and concentrated hydrochloric acid (5 ml) added. The resultant yellow solution was heated under reflux for 2 hours. On cooling, yellow needles of (Z)-3'-cyano-2-benzylidenebenzofuran-3(2H)-one m.p. 162° C. formed and were removed by filtration. The aurone (0.5 g, 0.0018 mole) and trimethyly silyl azide (1 g, 0.086 mole) were refluxed together in dimethylformamide for 6 hours. The cooled solution was poured into ice and hydrochloric acid. The suspension was then heated to 70° C. for 30 minutes and after cooling the precipitate was filtered off. This yellow oily solid, after chromatography, yielded the title compound, m.p. 242°-243° C.

EXAMPLE 43

(Z)-3'-Carboxyl-2-benzylidene-5-carbomethoxy-6-aminobenzofuran-3-(2H)-one

The methyl 3-acetyl-4-hydroxy-6-aminobenzoate (8.0 g, 0.038 mole) in dichloromethane (250 ml) was added to trifluoroacetic anhydride (16 g, 0.076 mole) and the solution stirred at room temperature of 15 minutes. On evaporation, the pale yellow solution yielded methyl 3-acetyl-4-acetoxy-6-trifluoroacetamidobenzoate, m.p. 130°-131° C.

Copper (II) bromide (17.0 g, 0.076 mole) was suspended in ethyl acetate (300 ml) by rapid stirring. To this suspension was added the benzoate produced above (11.5 g, 0.038 mole) as a solution in ethyl acetate (200 ml) and the resultant mixture was stirred and heated under reflux for 3 hours. The pale green cuprous bromide so formed was removed, after cooling, by filtration and the solution evaporated to give a pale yellow solid which was recrystallised from ether/petroleum ether (40°-60° C.) yielding methyl 3-bromoacetyl-4-acetoxy-6-trifluoroacetamidobenzoate as white crystals, m.p. 260°-261° C.

This compound (1.9 g, 0.005 mole) and 2-carboxybenzaldehyde (0.75 g, 0.005 mole) in methanol (100 ml) were then heated to 60° C. Sodium hydroxide (0.6 g, 0.015 mole) in water (20 ml) was slowly added to the stirred solution. The resultant red solution was heated under reflux for 3 hours and then poured on to ice and hydrochloric acid (5 M). The yellow solid so formed was filtered off and dissolved in aqueous sodium bicarbonate solution (10%) at 50° C. The pH of this solution was adjusted to 7 and Amberlite Resin IRA-401 in the hydroxyl form added. The resin was then filtered off and washed, firstly with water and then with glacial acetic acid. On concentration the acetic acid washings yielded the title compound as bright yellow prisms, m.p. 280° C. (decomp.).

EXAMPLE 44

(Z)-3'-Carboxyl-2-benzylidene-5,7-dibromo-4-hydroxybenzofuran-3(2H)-one

Finely ground copper (II) bromide (88 g, 0.4 mole) was suspended in a 50:50 mixture of ethyl acetate and chloroform (200 ml). 2,6-Dihydroxyacetophenone (10 g, 0.0657 mole) in chloroform (20 ml) was added to the above suspension which was stirred under reflux for 8 hours, hydrogen bromide being evolved. After cooling the copper (I) bromide formed in the above reaction was filtered off and the solution evaporated to dryness to give 3,5-dibromo-2,6-dihydroxy ω-bromoacetophenone (8.2 g, 0.21 mole) and sodium acetate (20 g) were refluxed in 90% ethanol (100 ml) for 15 minutes. On cooling and following the addition of water (100 ml), the yellow solution deposited a greenish solid which was recrystallised from ethanol/water to give 5,7-dibromo-4-hydroxybenzofuran-3(2H)-one, m.p. 185° C. (decomp.)

The benzofuran-3(2H)-one was then reacted with 3-carboxylbenzyaldehyde using the procedure described in Example 6 to yield the title compound, m.p. 300° C. decomp.)

EXAMPLES 45 AND 46

The following compounds were prepared by a method similar to Example 44 using the appropriate benzaldehyde.

(Z)-4'-Carboxyl-2-benzylidene-5,7-dibromo-4-hydroxybenzofuran-3(2H-one, m.p. 300° C. (decomp)

(Z)-2'Carboxyl-2-benzylidene-5,7-dibromo-4-hydroxybenzofuran-3(2H)-one, m.p. 258°-260° C.

EXAMPLE 47

(Z)-4'-[(E)-2-Carboxyvinyl]-2-benzylidene-6-amino-5-cyanobenzofuran-3(2H)-one

4-Amino-5-cyano-2-hydroxyacetophenone (J. C. S. Perkin I 1979 3 677) was converted into 4-trifluoroacetamido-5-cyano-2-hydroxyacetophenone (m.p. 214° C.) using the procedure described in Example 43.

This acetophenone was then brominated using copper (II) bromide by the method described in Example 44 to yield 4-trifluoroacetamido-5-cyano-2-hydroxybromoacetopheonone m.p. 202° C.

The ω-bromoacetophenone (3.8 g 0.011 mole) was dissolved in ethanol 50 ml and excess sodium acetate (10 g) added along with water (10 ml). The mixture was then refluxed for 20 minutes and on cooling deposited an orange solid which was recrystallised from ethanol water to yield orange plates of 6-amino-5-cyanobenzofuran-3(2H)-one, m.p. 270° C. (decomp)

This benzofuranone was then reacted with (E) 4-formylcinnamic acid using the procedure described in Example 6, the title compound being obtained as orange crystals, m.p. 300° C.

EXAMPLE 48

(Z)-3'-Carboxyl-2-benzylidene-5-cyclohexybenzofuran-3(2H)-one

4-Cyclohexyphenol (88 g, 0.5 mole) and acetyl chloride (39 g, 0.5 mole) were heated together at 170° C. for 3 hours. The clear liquid so formed was then cooled to 100° C. and aluminium chloride (133 g, 1.0 mole) added slowly. The brown sticky oil was then heated to 130° C. for 5 hours. After cooling, ice and hydrochloric acid were added and the phenol extracted with chloroform. This extract was then evaporated to dryness and the residue steam distilled to give 2-acetyl-4-cyclohexylphenol as a clear oil. This phenol was then reacted with copper (II) bromide using the procedure described in Example 43. This reaction yielding 2-bromoacetyl-4-cyclohexylphenol as a yellow oil. This oil was dissolved in ethanol (100 ml), and sodium acetate (44 g) and water (20 ml) added. This solution was then refluxed for 10 minutes, cooled and water added to deposit a brown oil which was extracted with chloroform. On evaporation to dryness the chloroform extract yielded the 5-cyclohexylbenzofuran-3(2H)-one which was then reacted with 3-carboxybenazldhyde using the procedure of Example 6 to yield the title compound as yellow crystals, m.p. 252°-253° C.

EXAMPLE 49

(Z)-3',4',5'-Trimethoxy-2-benzylidene-5-carboxybenzofuran-3(2H)-one (a) Methyl-4-acetoxybenzoate (126 g, 0.65 mole) and aluminium chloride (220 g, 1.63 mole) were intimately mixed, stirred and reacted at 160° C. by the method of G. Dora et al., Eur. J. Med. Chem 1978 13, 33. The crude solid product obtained after acid treatment was stirred with saturated sodium bicarbonate solution and the mixture filtered. The filtrate was carefully acidified to give 3-acetyl-4-hydroxybenzoic acid, which was filtered off, water washed and dried, m.p. 232° C.

The insoluble solid from the above bicarbonate extraction was dissolved in dilute sodium hydroxide (2 N) solution and carefully acidified with dilute hydrochloric acid (5 N) solution to give methyl 3-acetyl-4-hydroxybenzoate, which after filtration, water washing and drying, had m.p. 90°-92° C.

(b) 3-Acetyl-4-hydroxybenzoic acid (24.0 g. 0.133 mole) was dissolved in dioxane (400 ml) at 40° C. and bromine (7.2 ml, 0 14 mole) added dropwise with stirring. The colour soon faded and after 45 minutes the clear supernatant was decanted from some insoluble material and evaporated to give a light straw coloured solid, 3-bromoacetyl-4-hydroxybenzoic acid, m.p. 226° C.

(c) The product from (b) was dissolved in ethanol/water (350/70 ml), sodium acetate (30 g) added and the solution stirred at 60° C. for 10 minutes. The deep orange red solution was cooled to 10° C., stirred, and carefully acidified with 5 N hydrochloric acid solution. The resultant bright yellow solution was diluted with an equal volume of water and stored in a refrigerator overnight. The yellow crystalline solid was filtered off, washed with cold water and dried to give 5-carboxybenzofuran-3-(2H)one, with m.p. 204° C. (decomp.)

(d) 5-Carboxybenzofuran-3-(2H)one (3.56 g., 0.02 mole) and 3,4,5-trimethoxy benzaldehyde (3.92 g., 0.02 mole) were dissolved in warm dioxane (50 ml.), concentrated hydrochloric acid (10 ml) added and the mixture stirred and gently heated in a steam bath for 15 minutes. After cooling and the addition of an equal volume of water the yellow crystalline solid was filtered off, washed with water and dried. Recrystallisation from glacial acetic acid gave the title compound, m.p. 290° C.

EXAMPLES 50 TO 60

The following compounds were prepared by a method similar to that described in Example 49:

(Z)-2-Benzylidene-5-carboxybenzofuran-3-(2H)one, m.p. 280° C.

(Z)-4'-Chloro-2-benzylidine-5-carboxybenzofuran-3-(2H)one, m.p. > 300° C.

(Z)-2'-Chloro-4'-dimethylamino-2-benzylidine-5-carboxybenzofuran-3(2H)one. m.p. 275° C. (decomp)

(Z)-4'-Butyl-2-benzylidene-5-carboxybenzofuran-3-(2H)one, m.p. 252° C.

(Z)-4'-Dimethylamino-2-benzylidene-5-carboxybenzofuran-3-(2H)one, m.p. 295° C.

(Z)-4'-Methoxy-2-benzylidene-5-carboxybenzofuran-3-(2H)one, m.p. 300° C.

(Z)-4'-[(E)-2-Carboxyvinyl]-2-benzylidene-5-carboxybenzofuran3-(2H)one, m.p. > 300° C.

(Z)-3'-Carboxyl-4'-hydroxy-2-benzylidene-5-carboxybenzofuran-3-(2H)one, m.p. > 300° C.

(Z)-4'-Acetamido-2-benzylidene-5-carboxybenzofuran-3-(2H)one, m.p. > 300° C.

(Z)-3'-Trifluoromethyl-2-benzylidene-5-carboxybenzofuran-3-(2H)one, m.p. 264° C.

(Z)-3'-(N-Isopropylcarboxamido)-2-benzylidene-5-carboxy benzofuran-3-(2H)one, m.p. 300° C.

EXAMPLE 61

5-Carboxyl-6-hydroxybenzofuran-3-(2H)one (a) 5-Acetyl-2,4-dimethoxybenzoic acid (Ber. 41, 1607, 1908) (21.1 g, 0.094 mole) was stirred in dioxane (200 ml.) at room temperature and bromine (5 ml., ca 0.1 mole) was added dropwise. The bromine colour gradually disappeared over 30 minutes and the mixture was then gently warmed in a steambath for 30 minutes, cooled and the dioxane removed in vacuo. The solid product was treated with boiling ethyl acetate, filtered hot and the filtrate evaporated to give 5-bromoacetyl-2,4-dimethoxybenzoic acid, m.p. 236° C.

(b) The product from (a) (21.6 g., 0.071 mole) was stirred in dichloromethane (250 ml), cooled in an ice bath and boron tribromide (25 ml) added dropwise. The solution was then heated under reflux (water bath) for 4 hours. The mixture was cooled and poured onto ice (1 kg.). After removal of dichloromethane, the resultant pink solid was filtered off, water washed, sucked dry and dissolved in ethanol/water (200/80 ml).

Sodium acetate (25 g) was added and the solution warmed at 60° C. for 30 minutes. After cooling and the removal of ethanol in vacuo, further water (150 ml) was added. The solution was cooled in an ice bath and hydrochloric acid solution (5 N) added dropwise with stirring to pH2. After overnight storage in a refrigerator the pale yellow crystalline solid was filtered off, water washed and dried to give the title benzofuranone, m.p. 216° C.

EXAMPLE 62

(Z)-3'-Carboxyl-2-benzylidene-5-carboxyl-6-hydroxybenzofuran-3-(2H)one 5-carboxy-6-hydroxybenzofuran-3-(2H)one (5.82 g, 0.03 mole) was dissolved in dioxane (75 ml), 3-carboxybenzaldehyde (4.50 g., 0.03 mole) added, followed by concentrated hydrochloric acid (15 ml). The solution was gently heated on a steam bath for 30 minutes with occasional stirring. The solid mixture was cooled, diluted with an equal volume of water and stored in a refrigerator for 1 hour. The product was filtered off, water washed and dried. Recrystallisation from dimethylformamide gave the desired compound with m.p. 335° C. (decomp).

EXAMPLES 63 AND 64

The following compounds were prepared by a similar method to that described in Example 62.

(Z)-3'-Carboxyl-4-hydroxy-2-benzylidene-5-carboxyl-6-hydroxy benzofuran-3-(2H)one, m.p. 332° C. (decomp.)

(Z)-4'-(Tetrazol-5-yl)-2-benzylidene-5-carboxyl-6-hydroxy benzofuran-3-(2H)one. m.p. 327°-28° C. (de comp.)

EXAMPLE 65

(Z)-3'-Carboxyl-2-benzylidene-5-methoxycarboxylbenzofuran-3-(2H)one

Methyl-3'-acetyl-4-hydroxy benzoate (5.39 g 0.028 mole) was stirred in dioxan (200 ml) at 40° C. and bromine (1.5 ml) added dropwise. After 45 minutes the colourless solution was evaporated to give a straw coloured oil which was dissolved in ethanol/water (75/15 ml.). Sodium acetate (6.0 g) was added and the solution stirred at room temperature for 5 minutes. The red solution was poured on to ice (100 g) and extracted via chloroform. Evaporation of the chloroform extract gave 5-methoxycarbonylbenzofuran-3-(2H)one as an orange red oil (65% pure by NMR).

This product was immediately dissolved in dioxane (50 ml.), 3-carboxybenzaldehyde (4.5 g., 0.03 mole) added, followed by concentrated hydrochloric acid (10 ml) and the solution heated on a steam bath for 15 minutes. Work up was as Example 49 with recrystallisation from dimethylformamide to give the desired aurone, m.p. 280° C.

EXAMPLE 66

(Z)-3'-Carboxyl-2-benzylidene-6-acetamidobenzofuran-3-(2H)-one (a) 3-Aminophenol (54.5 g., 0.05 mole) and acetic anhydride (200 ml) were stirred and heated on a steam bath for 2 hours. The straw coloured liquid was evaporated in vacuo to give a viscous oil which was heated to 110°-120° C. aluminium chloride (170 g. 1.27 mole) being added gradually with stirring. After 30 minutes the solid product was cooled somewhat and carefully decomposed with ice/water (ca 500 g.) followed by concentrated hydrochloric acid (200 ml.), stirred well and warmed slightly on steam bath. On cooling, the crystaline solid was filtered off, water washed and dried to give the desired compound 2-hydroxy-4-acetamidoacetophenone, m.p. 40° C.

(b) The product from (a) (14.0 g 0.072 mole) was dissolved in ethyl acetate (300 ml) and added to a stirred suspension of copper (II) bromide (32 g. 0.142 mole) in ethyl acetate (100 mole). The mixture was heated under reflux for 4 hours, then filtered hot and the filtrate evaporated in vacuo to give an oil which crystallised. This solid was converted to the benzofuranone and reacted with 3-carboxybenzaldehyde (as Example 65). However, during this reaction the product was partially deacylated and it was further reacted with acetic anhydride (20 ml) under reflux to convert to the fully acehylated compound. The reaction mixture was poured onto ice (100 g) and the excess acetic anhydride hydrolysed. The resulant solid was filtered off and recrystallised from glacial acetic acid/water (50% v/v) to give (Z)-3'-carboxyl-2-benzylidene-6-acetamidobenzofuran-3-(2H)one, m.p. 305° C. (decomp.)

EXAMPLE 67

(Z)-4'-Chloro-2-benzylidene-5-n-butoxycarbonyl benzofuran-3-(2H)one

Z-4'-Chloro-2-benzylidene-5-carboxybenzofuran-3-(2H)one (3.0 g. 0.01 mole) was suspended in n-butanol (50 ml), concentrated sulphuric acid (1.5 ml) added dropwise with stirring and the mixture heated under reflux for 5 hours. The resultant yellow solution on cooling deposited yellow fluffy needle crystals of the desired n-butyl ester. The crystals were filtered off, washed with cold n-butanol, then diethylether and dried, m.p. 154° C.

EXAMPLE 68

(E)-4'-Chloro-2-benzylidene-5-n-butoxycarbonylbenzofuran 3-(2H)one (Z)-4'-Chloro-2-benzylidene-5-n-butoxycarbonylbenzofuran 3-(2H)one (1.0 g) was dissolved in benzene (800 ml) and irradiated in a 1 liter Hanovia photochemical reactor for 15 hours. The solution was evaporated in vacuo to give 1.0 g of solid with m.p. ca 130° and having an E/Z isomer ratio of 75/25 (based on NMR and HPLC). 500 mg of this solid was chromatographed on a Sorbsil silica gel column (200 g.) using benzene as the developing solvent and the fractions containing the faster moving (E)-isomer collected. These fractions were bulked and evaporated to give a yellow crystalline solid; yield 350 mg. of mp 142° C. and having an E/Z isomer ratio of 88/12.

200 mg. this solid was recrystallised from dichloromethane/40°-60° C. petroleum ether (⅓ v/v) to give 130 mg. of crystalline solid of m.p. 142° and having an E/Z isomer ratio of 95.5/7.5.

The following formulations were prepared using as active ingredient the compound (Z)-3'-carboxyl-2-benzylidene-5-chlorobenzofuran-3-(2H)-one, and similar formulations can be prepared with other solid compounds of the invention.

EXAMPLE 69

Hard gelatin capsules were prepared using the following ingredients:

| | Quantity (mg/capsule) |
|---|---|
| Active compound | 250 |
| Starch dried | 200 |
| Magnesium stearate | 10 |

The above indredients were mixed and filled into hard gelatin capsules

EXAMPLE 70

A tablet formula was prepared using the ingredients below:

| | Quantity (mg/tablet) |
|---|---|
| Active compound | 250 |
| Cellulose microcrystalline | 400 |
| Silicon dioxide fumed | 10 |
| Stearic acid | 5 |

The components were blended and compressed to form tablets.

EXAMPLE 71

An aerosol solution was prepared containing the following components:

| | Weight % |
|---|---|
| Active ingredient | 0.25 |
| Ethanol | 29.75 |
| Propellant 22 (Chlorodifluoromethane) | 70 |

The active compound was mixed with ethanol and the mixture added to the propellant 22, cooled to −30° C. and transferred to a filling device. The required amount was then fed to a stainless steel container and diluted further with a metered amount of propellant. The valve units were then fitted to the container.

EXAMPLE 72

A suppository formula was prepared containing 200 mg of the compound using the following ingredients:

| | |
|---|---|
| Active compound | 200 mg |
| Polyethylene glycol 1000 | 750 mg |
| Polyethylene glycol 4000 | 250 mg |

The active compound was mixed in the molten glycol bases and then the mixture was poured into appropriate suppository moulds, to give the active fill weight.

EXAMPLE 73

An ointment was made to the following formula:

| | |
|---|---|
| Active compound | 1% by weight |
| White soft paraffin | up to 100% |

The active compound was added to the molten paraffin and then the mixture was allowed to cool.

What we claim is:

[1. A compound of the formula

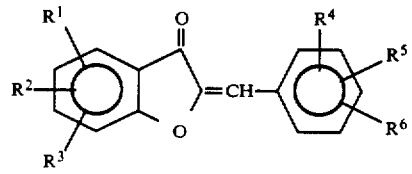

in which in which $R^1$,$R^2$,$R^3$,$R^4$,$R^5$ and $R^6$ are the same or different and can each represent hydrogen, halogen, $C_{1-6}$ alkyl, $C_{1-6}$ alkoxy, $C_{3-8}$ cycloalkyl, optionally substituted phenyl, $C_{1-6}$ haloalkyl, amido, amino, cyano, hydroxy, nitro, $C_{2-4}$ alkenyl, carboxyl, tetrazol-5-yl or —CH=CHCOOH; or in which $R^1$ and $R^2$ taken together represent a group of formula —CH=

CH—CH=CH—; provided that at least one of $R^1,R^2,R^3,R^4,R^5$ and $R^6$ is carboxyl, tetrazol-5-yl or —CH=CHCOOH; or a pharmaceutically-acceptable salt or ester thereof.]

[2. A compound of the formula

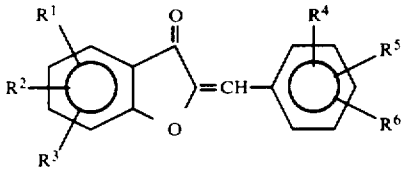

in which $R^1,R^2,R^3$, $R^4,R^5$ and $R^6$ are the same or different and can each represent hydrogen, halogen, $C_{1-6}$ alkyl, $C_{1-6}$ alkoxy, $C_{3-8}$ cyloalkyl, optionally substituted phenyl, $C_{1-6}$ haloalkyl, amido, amino, cyano, hydroxy, nitro, $C_{2-4}$ alkenyl, carboxyl, tetrazol-5-yl or —CH=CHCOOH; or in which $R^1$ and $R^2$ taken together respresent a group of formula —CH=CH—CH=CH—; provided that at least one of $R^1,R^2,R^3,R^4,R^5$ and $R^6$ is carboxyl, tetrazol-5-yl or —CH=CHCOOH, and at least one of $R^1,R^2$ and $R^3$ is other than hydrogen; or a pharmaceutically-acceptable salt or ester thereof.]

3. A compound according to claim [2] *20* in which $R^1$ is $C_{1-4}$ alkyl, carboxyl or halogen, $R^2$ and $R^3$ are hydrogen, $R^4$ is carboxyl or —CH=CHCOOH, and $R^5$ and $R^6$ are hydrogen.

4. A compound according to claim [2] *3* in which $R^1$ is $C_{1-4}$ alkyl or carboxyl, $R^2$ and $R^3$ are hydrogen, $R^4$ is carboxyl or —CH=CHCOOH, and $R^5$ and $R^6$ are hydrogen.

[5. A compound of the formula

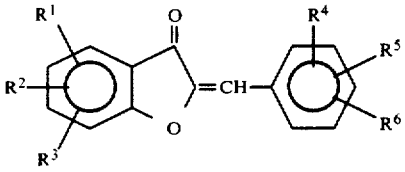

in which $R^1,R^2,R^3,R^4,R^5$ and $R^6$ are the same or different and can each represent hydrogen, halogen, $C_{1-6}$ alkyl, $C_{1-6}$ alkoxy, $C_{3-8}$ cycloalkyl, optionally substituted phenyl, $C^{1-6}$ haloalkyl, amido, amino, cyano, hydroxy, nitro, $C_{2-4}$ alkenyl, carboxyl, tetrazol-5-yl or —CH=CHCOOH; or in which $R^1$ and $R^2$ taken together represent a group of formula —CH=CH—CH=CH—; provided that at least one of $R^1,R^2,R^3,R^4,R^5$ and $R^6$ is carboxyl, tetrazol-5-yl or —CH=CHCOOH and at least one of $R^4,R^5$ and $R^6$ is halogen, $C_{3-8}$ cycloalkyl, optionally substituted phenyl, C1-6 haloalkyl, amido, cyano, nitro, carboxyl, tetrazol-5-yl or —CH=CHCOOH, or a pharmaceutically acceptable salt or ester thereof.]

6. A compound according to claim 5] *20* in which at least one of $R^1,R^2$ and $R^3$ is other than hydrogen.

[7. A compound according to claim 5 in which one of $R^4,R^5$ or $R^6$ is carboxyl, tetrazol-5-yl or —CH=CH—COOH.]

8. A process for preparing a compound according to claim [1] *16* wherein [$R^1,R^2,R^3$,] $R^4$, [$R^5$ or $R^6$are] *is* other than tetrazol-5-yl which comprises reacting a benzaldehyde of the formula

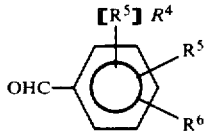

with a reactant of the formula

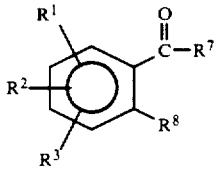

wherein $R^7$ when taken singly is $CH_2X$;
wherein X is a leaving group; and
$R^8$ when taken singly is OH; and
$R^7$ and $R^8$ taken together form the group —$CH_2$—O—.

9. A process for preparing a compound according to claim [1] *16* wherein [one of $R^1$, $R^2$, $R^3$,] $R^4$, [$R^5$ or $R^6$] is tetrazol-5-yl which comprises reacting a benzaldehyde of the formula

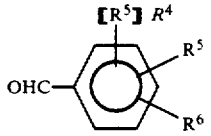

with a reactant of the formula

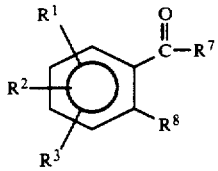

wherein $R^7$ when taken singly is $CH_2X$;
wherein X is a leaving group, $R^8$ when taken singly is OH and $R^7$ and $R^8$ when taken together are —$CH_2$—O—
wherein [one of $R^1,R^2,R^3$,] $R^4$,[$R^5$ or $R^6$] is cyano, and then reacting the aurone thus formed containing a cyano group with an azide to form the corresponding tetrazol-5-yl substituted aurone.

10. A pharmaceutical formulation *in unit dosage form* for use in treating immediate hypersensitivity conditions such as asthma which comprises as an active ingredient an effective amount of a compound according to claim [1] *16* associated with a pharmaceutically-acceptable carrier therefor.

11. A pharmaceutical formulation *in unit dosage form* for use in treating immediate hypersensitivity conditions such as asthma which comprises as an active ingredient an effective amount of a compound according to claim [2] *17* associated with a pharmaceutically-acceptable carrier therefor.

12. A pharmaceutical formulation *in unit dosage form* for use in treating immediate hypersensitivity conditions such as asthma which comprises as an active ingredient an effective amount of a compound according to claim [5] *20* associated with a pharmaceutically-acceptable carrier therefor.

13. A method of prophylactic chemotherapy of immediate hypersensitivity conditions such as asthma which comprises administering to a human susceptible to such conditions a prophylactically effective amount of a compound according to claim [1] *16*.

14. A method of prophylactic chemotherapy of immediate hypersensitivity conditions such as asthma which comprises administering to a human susceptible to such conditions a prophylactically effective amount of a compound according to claim [2] *17*.

15. A method of prophylactic chemotherapy of immediate hypersensitivity conditions such as asthma which comprises administering to a human susceptible to such conditions a prophylactically effective amount of a compound according to claim [5] *20*.

*16. A compound of the formula*

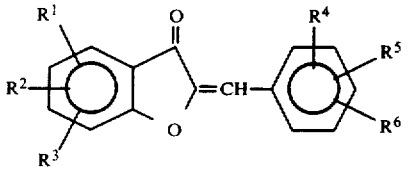

*in which $R^1$, $R^2$, $R^3$, $R^5$ and $R^6$ are the same or different can each represent hydrogen, halogen, $C_{1-6}$alkyl, $C_{1-6}$alkoxy, $C_{3-8}$cycloalkyl, optionally substituted phenyl, $C_{1-6}$haloalkyl, amido, amino, cyano, hydroxy, nitro or $C_{2-4}$alkenyl, and $R^4$ is carboxyl, tetrazol-5-yl or —CH=CHCOOH; or in which $R^1$ and $R^2$ taken togehter represent a group of the formula —CH=CH—CH=CH; or a pharmaceutically-acceptable salt or ester thereof.*

*17. A compound of the formula*

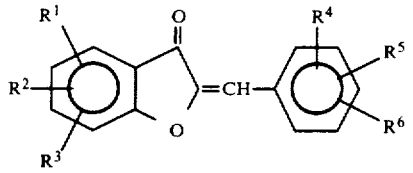

*in which $R^1$, $R^2$, $R^3$, $R^5$ and $R^6$ are the same or different and can each represent hydrogen, halogen $C_{1-6}$alkyl, $C_{1-6}$alkoxy, $C_{3-8}$cycloalkyl, optionally substituted phenyl, $C_{1-6}$haloalkyl, amido, amino, cyano, hydroxy, nitro or $C_{2-4}$alkenyl, and $R^4$ can be carboxyl, tetrazol-5-yl or —CH=CHCOOH; or in which $R^1$ and $R^2$ taken together represent a group of the formula —CH=CH—CH=CH—; provided that at least one of $R^1$, $R^2$ and $R^3$ is other than hydrogen; or a pharmaceutically-acceptable salt or ester thereof.*

*18. A compound according to claim 17 in which $R^1$ is $C_{1-4}$alkyl, $C_{1-4}$alkoxy or halogen, $R^4$ is carboxyl or —CH=CHCOOH, and $R^2$, $R^3$, $R^5$ and $R^6$ are hydrogen.*

*19. A compound according to claim 18 in which $R^1$ is $C_{1-4}$alkyl, $R^4$ is carboxyl or —CH=CHCOOH, and $R^2$, $R^3$, $R^5$ and $R^6$ are hydrogen.*

*20. A compound of the formula*

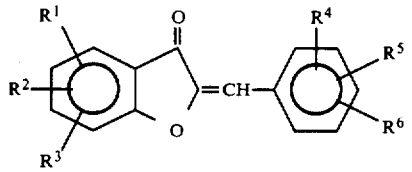

*in which $R^1$, $R^2$, $R^3$, $R^5$ and $R^6$ are the same or different and can each represent hydrogen, carboxyl, tetrazol-5-yl, —CH=CHCOOH, halogen, $C_{1-6}$alkyl, $C_{1-6}$alkoxy, $C_{3-8}$cycloalkyl, optionally substituted phenyl, $C_{1-6}$haloalkyl, amido, amino, cyano, hydroxy, nitro or $C_{2-4}$alkenyl and $R^4$ is carboxyl, tetrazol-5-yl or —CH=CHCOOH; or in which $R^1$ and $R^2$ taken together represent a group of the formula —CH=CH—CH=CH—; or a pharmaceutically-acceptable salt or ester thereof.*

* * * * *